United States Patent [19]

Scheller

[11] 4,223,003
[45] Sep. 16, 1980

[54] PASTE AND POWDER DENTIFRICES

[75] Inventor: Hans-Ulrich Scheller, Uhingen, Fed. Rep. of Germany

[73] Assignee: Württembergische Parfumerie-Fabrik GmbH, Eislingen, Fed. Rep. of Germany

[21] Appl. No.: 31,717

[22] Filed: Apr. 20, 1979

[51] Int. Cl.² .......................... A61K 7/16; A61K 7/18; A61K 7/20; A61K 7/22

[52] U.S. Cl. .......................................... 424/7; 424/49; 424/52; 424/53; 424/54; 424/56; 424/57; 424/58

[58] Field of Search ................................ 424/7, 49–58

[56] References Cited

U.S. PATENT DOCUMENTS

| | | | |
|---|---|---|---|
| 1,112,180 | 9/1914 | Westenfelter | 424/7 |
| 1,717,723 | 6/1929 | McCall | 424/7 |
| 2,054,742 | 9/1936 | Elbel | 424/53 |
| 2,151,495 | 3/1939 | Bender | 424/7 |
| 3,137,632 | 6/1964 | Schiraldi | 424/49 |
| 3,309,274 | 3/1967 | Brilliant | 424/7 |
| 3,903,252 | 9/1975 | Stearns | 424/7 |
| 4,064,229 | 12/1977 | Block | 424/7 |
| 4,071,614 | 1/1978 | Grimm | 424/49 |
| 4,093,711 | 6/1978 | Blackburne et al. | 424/54 |
| 4,150,106 | 4/1979 | Assal et al. | 424/7 |

FOREIGN PATENT DOCUMENTS

| | | | |
|---|---|---|---|
| 2410573 | 9/1975 | Fed. Rep. of Germany | 424/49 |
| 2416272 | 10/1975 | Fed. Rep. of Germany | 424/7 |
| 944506 | 4/1949 | France | 424/53 |
| 2203618 | 5/1974 | France | 424/7 |
| 327823 | 7/1935 | Italy | 424/7 |
| 49-66837 | 6/1974 | Japan | 424/49 |
| 51-38427 | 9/1974 | Japan | 424/7 |
| 51-38428 | 9/1974 | Japan | 424/7 |
| 51-38429 | 9/1974 | Japan | 424/7 |
| 423858 | 2/1935 | United Kingdom | 424/7 |
| 1234422 | 6/1971 | United Kingdom | 424/53 |
| 1381444 | 1/1975 | United Kingdom | 424/7 |

OTHER PUBLICATIONS

Schwartz et al., Surface Active Agents and Detergents, vol. II, pp. 75–76, 550–552, 557–562, 620–621, (1958), Interscience Publishers, Inc., N.Y., N.Y.

Reng, A. K., Parfuem Kosmet, v. 57(11):307–316, (1976), Foaming Agents for Products for Oral and Dental Hygiene (Hoechst A/G).

Primary Examiner—Shep K. Rose
Attorney, Agent, or Firm—Sprung, Felfe, Horn, Lynch & Kramer

[57] ABSTRACT

A dentifrice in paste or powder form which contains, in addition to the usual constituents, at least one physiologically compatible, natural or synthetic dye and at least one high-foam surfactant and in which the dye and surfactant contents are so co-ordinated that colored foam produced by the user on brushing takes 20 seconds or more to become white or only pale in color so that this serves as an indication of the correct period of brushing necessary.

8 Claims, No Drawings

PASTE AND POWDER DENTIFRICES

This invention relates to improved dentifrices particularly in paste and powder form containing dyes and surfactants.

Dye-containing dentifrices are known. For example, dyes are incorporated into some toothpastes which provide the white strand of toothpaste applied to the toothbrush with colored stripes or produce a completely colored strand of toothpaste. Toothpastes such as these normally contain soluble dyes in quantities of from 0.001 to 0.02% by weight and surfactants in quantities of from 1 to 2% by weight. The object of this measure is to provide the toothpaste with an aesthetically better appearance. This applies in particular to transparent toothpastes which may even have a dye content of more than 0.02% by weight, depending on the type of dye used. In the practical application of a toothpaste such as this, a white or faintly colored foam is developed, but does not undergo any significant change in color during cleaning.

The object of the present invention is on the contrary to provide the user of the dentifrice with an indication of an adequate cleaning time through fading of the added dye. In general, dentifrices take a certain time to develop their effect. This applies in particular to dentifrices containing special active ingredients, for example vegetable extracts, solvents such as alcohol, propylene glycol and the like, peroxide compounds or the like, and also to toothpastes having a low abrasive activity. The cleaning effect of a dentifrice is also governed by the intensity of the cleaning movements made with the toothbrush, so that the time required to obtain an adequate cleaning effect can differ according to the temperament of the user or even according to whether an ordinary toothbrush or an electrical toothbrush is used. However, since experience has shown that most people lose all sense of time when cleaning teeth, the optimum cleaning time is frequently not reached. Thus, a period of only 20 seconds can seem a long time when cleaning teeth. However, a minimum period of 30 seconds is regarded as desirable for cleaning teeth. Some dentists even recommend cleaning times of 1 to 2 minutes. Accordingly, the object of the present invention is to provide a dentifrice which automatically indicates the optimum cleaning time required through an optical effect which can be observed by the user in the bathroom mirror.

This object is achieved by using dyes together with high-foam surfactants in dentifrices, the dye and surfactant being co-ordinated with one another in such a way that, when the dentifrice in question is used, it generates a colored foam which loses its color either completely or to a considerable extent only after an adequate cleaning time, i.e. at the earliest after 20 seconds.

The present invention therefore provides a dentifrice in paste or powder form containing, at least one physiologically compatible, natural or synthetic dye and at least one high-foam surfactant, in which the dye and surfactant contents are co-ordinated with one another in such a way that, when the teeth are vigorously and continuously cleaned with a toothbrush, the colored foam generated by the dentifrice at the beginning of cleaning takes 20 seconds or longer to become white or only pale in color.

Toothpastes with the usual, comparatively small, amount of dye are only capable of producing a white foam or only a pale-colored foam which immediately loses its color. The foam generated by toothpastes having a relatively high dye content shows a permanent color because of the usually low surfactant content. In this case, no significant change in color occurs within the normal cleaning times. By contrast, it has now been found that, at the beginning of cleaning, toothpastes having a high dye content and a correspondingly adapted surfactant content generate a colored foam which gradually loses its color or distinctly fades with increasing cleaning time, depending on the type and quantity of dyes added. This optically visible change in color is caused by the foaming of the toothpaste and, hence, on the one hand by its surfactant content and, on the other hand, by the intensity of the cleaning movements made with the toothbrush. If, now, the surfactant content of the dentifrice is adjusted accordingly and co-ordinated with the dye content, the described change in color occurs at the earliest after 20 seconds, even with intensive cleaning movements. Depending on the type and concentration of the two critical components, the onset of this effect can be delayed to such an extent that cleaning times of from 20 to 120 seconds are obtained. The maximum cleaning time of 120 seconds indicated only represents an arbitrary limit because experience has shown that longer times are generally not required for cleaning teeth.

The lightening in color or decoloring of the foam during cleaning may be characterized by determining the lightness L of the particular color because, irrespective of the type of color, the difference $\Delta L$ obtained provides an indication of the amount of dye which the dentifrice has to contain to obtain a significnant change in color in dependence upon the surfactant content. Normally a color can be defined in regard to hue and saturation by the standard color value components x and y. However, the two-dimensional representation of a color plane derived from these standard color value components (Standard Color Table according to DIN No. 5033) says nothing about the lightness of a color because colors of the same type can differ in their lightness. The lightness of a color has to be defined by an additional quantity L which amounts to 100 for white and to 0 for black. In the L,a,b-color diagram according to the CIE-L-,a-,b-system, the lightness axis L stands perpendicularly on the a,b-color plane, cf. in particular "Ullmanns Encyklopadie der technischen Chemie", 4th Edition, Vol. 11, pages 179 to 183.

According to the invention, the lightness differences $\Delta L$ are best determined by means of color comparison tables. To this end, the color tables corresponding to the foams to be compared with one another are first determined and $\Delta L$ subsequently measured. The differences in lightness may be measured by means of a spectral filter photometer, for example by means of a colorimeter of the type manufactured by the Hunterlab company. Thus, the following lightness difference values were determined for example for the lightening of the foam generated by differently colored dentifrices according to the invention:

| | |
|---|---|
| Change in color from blue to light blue (almost white) | $\Delta L = 15.24$ |
| Change in color from dark blue to light blue | $\Delta L = 25.55$ |
| Change in color from green to yellow | $\Delta L = 19.60$ |
| Change in color from chlorophyll | |

| green light green (almost white) | ΔL = 19.95 |
| --- | --- |

The measured differences in lightness are in a range from L=60 to 100 because in each case the colored foam becomes white or pale in color.

Accordingly, the invention preferably relates to dentifrices of which the dye content—for a surfactant content of at least 2.5% by weight, based on the total weight of the dentifrice—is measured in such a way that a difference in lightness Δ L in the range of about 10 to 30 and more particularly in the range of about 15 to 25 occurs during lightening of the foam. A difference in lightness Δ L in the region of 20 is particularly preferred. The content of high-foam surfactants in the dentifrice should amount to between about 2.5% by weight and 8% by weight. Depending upon the dye content and the depth of color of the dye selected, the preferred surfactant content ranges from about 4 to 6% by weight.

The amount of dye required to obtain a significant lightening in color of the foam is determined not only by the surfactant content, but also by the type of dye used. The quantities of dye for which the foam lightens or fades within certain cleaning period may differ according to the hue and saturation of the dye. For example, a content of only 0.003% by weight of the food dye Blau ZN3 (Colour Index: 42051, EG-No. 131) in a dentifrice containing approximately 5% by weight of surfactants produces a distinctly visible effect, i.e. the initially colored foam only fades after a certain time. The quantity of this dye may be increased to 0.012% by weight, although in that case the foam does not completely lose its color, even with a fairly long cleaning time. In the case of the dye Blau ZN 3, therefore, a content in the range from 0.004 to 0.006% by weight is preferred for the dentifrices according to the invention, whereas other dyes will be used in other ranges.

Physiologically compatible dyes suitable for the purposes of the invention are any natural or synthetic dyes of the type permitted in foods. Preferred dyes are red, blue and/or green dyes of the type belonging to Classes III/2 and IV/2 of the Common Market Directive (1977). In addition to the food dye Blue ZN 3 which has already been mentioned, the following dyes are mentioned as examples of suitable dyes:

| L-Red ZN 3, Colour Index 16 185, | EG-No. 123 |
| --- | --- |
| L-Red ZN 4, Colour Index 45 430, | EG-No. 127 |
| Lemon Yellow ZN 3, Colour Index 47 005, | EG-No. 104 |
| Chlorophyll, Colour Index 75 810, | EG-No. 140 |
| Indanthrene Blue, Colour Index 69 800, | EG-No. 130. |

In addition to these water-soluble dyes, however, it is also possible to use water-insoluble dyes, for example Eyeshadow Blue KO, Colour Index 77 510, EG-No. Blue 15 (C-Blue 17), or even mixtures of water-insoluble dyes and water-soluble dyes, for example Eyeshadow Blue KO with Lemon yellow ZN 3, in which case green hues are obtained.

Surfactants suitable for the purpose of the invention are any of the washing-active substances normally used in dentifrices which have a high foaming power and which are relatively stable to the salts responsible for the hardness of water. Preferred compounds are alkali metal salts of primary alkyl sulphates (fatty alcohol sulphates), of alkane sulphonates, of condensation products of fatty acids and amino alkane sulphonic acids (fatty acids (methyl) taurides) and/or amine oxides. In view of the high foaming power which is essential for a significant lightening in color of the foam, it is particularly preferred to use a mixture of the sodium salt of lauryl alcohol sulphate and the sodium salt of myristic acid tauride in a ratio by weight of about 3:2 as the surfactant.

The dentifrices according to the invention will usually contain the constituents normally present in toothpastes and tooth powders, including abrasives and polishes, binders and thickeners, humectants, flavorings and sweeteners and also special active ingredients, such as for example fluorine compounds, bacteriostatic agents or the like. In addition, the dentifrices according to the invention preferably contain medicinally active substances which take at least 20 seconds and, in particular, at least 30 seconds to develop their effect. Substances such as these include, for example, substances for removing films from teeth, vegetable extracts, allantoin or peroxide-containing substances, such as magnesium peroxide. A toothpaste containing magnesium peroxide is mentioned as one example of this. Where a toothpaste such as this is used, the evolution of oxygen only begins after a cleaning time of about 15 seconds. After about 60 seconds, only about 20% of the peroxide has decomposed:

| Seconds | 30 | 60 | 120 | 180 |
| --- | --- | --- | --- | --- |
| Oxygen liberated: | 18% | 22% | 25% | 26% |

This example shows that the active ingredient can only develop its effect over a relatively long cleaning time. The type and quantity of constituents such as these are shown in the following examples which illustrate formulations for dentifrices according to the invention:

EXAMPLE 1

| Substance | Quantity in % by weight | Preferably |
| --- | --- | --- |
| Blue ZN 3 | 0.004–0.006 | 0.005 |
| Flavorings | 0.3–5 | 0.8 |
| Pyrogenic silica | 1–5 | 3.5 |
| Carboxymethyl cellulose | 0.5–2.5 | 1 |
| Bromochlorophene | 0.01–0.1 | 0.05 |
| Dicalcium phosphate | 20–35 | 28 |
| Sodium lauryl alcohol sulphate | 1–5 | 3 |
| Sodium myristic acid tauride | 0.3–3 | 2 |
| Glycerol (86%) or sorbitol | 5–30 | 6 |
| Sodium p-hydroxybenzoic acid methyl ester | 0.05–0.2 | 0.14 |
| Sodium monofluorophosphate | 0.1–0.8 | 0.76 |
| Demineralized water | ad 100 | |

EXAMPLE 2

| Substance | Quantity in % by weight | Preferably |
| --- | --- | --- |
| Augenlider Blue Ko | 0.02–0.04 | 0.03 |
| Lemon Gel ZN 3 | 0.1–0.3 | 0.2 |
| Flavorings | 0.3–5 | 3 |
| Pyrogenic silica | 1–5 | 2.5 |
| Carboxymethyl cellulose | 0.5–2.5 | 1 |
| Calcium carbonate | 10–30 | 20 |
| Dicalcium phosphate | 5–15 | 12 |

-continued

| Substance | Quantity in % by weight | Preferably |
|---|---|---|
| Sodium lauryl alcohol sulphate | 1-5 | 3 |
| Sodium myristic acid tauride | 0.3-3 | 2 |
| Sodium p-hydroxybenzoic acid methyl ester | 0.05-0.2 | 0.14 |
| Glycerol (86%) or sorbitol | 5-30 | 12 |
| Demineralized water | ad 100 | |

EXAMPLE 3

| Substance | Quantity in % by weight | Preferably |
|---|---|---|
| Blue ZN 3 | 0.004-0.006 | 0.005 or |
| Indanthrene (dye paste) | 0.050-0.062 | 0.0575 |
| Dicalcium phosphate | 10-30 | 22 |
| Sodium lauryl alcohol sulphate | 1-5 | 3 |
| Sodium myristic acid tauride | 0.3-3 | 2 |
| Pyrogenic silica | 2-10 | 6 |
| Polyvinyl pyrrolidone | 0.1-3 | 0.5 |
| Magnesium peroxide | 1-10 | 4 |
| Disodium hydrogen pyrophosphate | 3-10 | 6 |
| Flavorings | 0.5-5 | 1 |
| Propylene glycol and/or glycerol, ethanol, isopropanol, n-propanol | ad 100 | |

EXAMPLE 4

| Substance | Quantity in % by weight | Preferably |
|---|---|---|
| Dicalcium phosphate | 10-30 | 22 |
| Sodium lauryl alcohol sulphate | 1-5 | 3 |
| Sodium myristic acid tauride | 0.3-3 | 2 |
| Pyrogenic silica | 2-10 | 6 |
| Polyvinyl pyrrolidone | 0.1-3 | 0.5 |
| Magnesium peroxide | 1-10 | 4 |
| Disodium hydrogen phosphate | 3-10 | 6 |
| Neem extract (vegetable extract) | 0.1-0.5 | 0.25 |
| Chlorophyll (50%) | 0.5-2 | 1 |
| Flavorings | 0.5-5 | 1 |
| Propylene glycol | ad 100 | |

EXAMPLE 5

| Tooth Powder: Substance | Quantity in % by weight |
|---|---|
| Anhydrous dicalcium phosphate | 20 |
| Polymethyl methacrylate powder | 15 |
| Polyvinyl chloride powder | 8 |
| Sodium lauryl alcohol sulphate | 3 |
| Sodium myristic acid tauride | 2 |
| Dyes | 0.02 |
| Flavorings | 1 |
| Fluorohexidine hydrochloride | 4.5 |
| Dicalcium phosphate dihydrate | 46.5 |

The effect of the dentifrices according to the invention in regard to fading of the foam generated is shown by the following comparison tests which were carried out with toothpastes corresponding to Example 3 having different dye contents. These comparison tests were conducted by five people using an electrical toothbrush (AEG Princesse). A 2 cm strand of toothpaste (corresponding to 0.5 g) was applied to a wetted toothbrush and cleaning continued until the originally distinctly blue foam was white or until there was no further change in color over a reasonable cleaning time.

Comparison Test A

Dye content: 0.0036% by weight of Blue ZN 3.

After cleaning times of 30 to 40 seconds, the originally blue-white foam was completely white; the measured difference in lightness Δ L amount to 15.24.

| 1st Test Person | after 30 seconds | white |
|---|---|---|
| 2nd Test Person | after 30 seconds | white |
| 3rd Test Person | after 40 seconds | white |
| 4th Test Person | after 40 seconds | white |
| 5th Test Person | after 30 seconds | white |
| | average time = 34 seconds | |

Comparison Test B

Dye content: 0.006% by weight of Blue ZN 3.

After cleaning times of from 90 to 100 seconds, the initially bright blue foam was almost completely white with a faint green shimmer; the measured difference in lightness Δ L amounted to 21.72.

| 1st Test Person | after 100 seconds | white |
|---|---|---|
| 2nd Test Person | after 90 seconds | white |
| 3rd Test Person | after 80 seconds | white |
| 4th Test Person | after 100 seconds | white |
| 5th Test Person | after 90 seconds | white |
| | average time = 92 seconds | |

Comparison Test C

Dye content: 0.012% by weight of Blue ZN 3.

After cleaning times of up to 2.5 minutes, the initially dark blue foam was still distinctly blueish in color. Complete decoloration could not be achieved in reasonable cleaning times; the measured difference in lightness Δ L amounted to 25.55.

| 1st Test Person | after 120 seconds | blue-white (no further change in color) |
|---|---|---|
| 2nd Test Person | after 150 seconds | blue-white (no further change in color) |
| 3rd Test Person | after 120 seconds | blue-white (no further change in color) |
| 4th Test Person | after 120 seconds | blue-white (no further change in color) |
| 5th Test Person | after 120 seconds | blue-white (no further change in color) |
| | average time = 126 seconds. | |

It will be appreciated that the instant specification and examples are set forth by way of illustration and not limitation, and that various modifications and changes may be made without departing from the spirit and scope of the present invention.

What is claimed is:

1. In the method of tooth brushing with dyed paste or powder dentifrice containing a physiologically compatible dye and at least 2.5 weight % of a high-foam surfactant, the improvement whereby fading of the original color as observable by the user in a bathroom mirror automatically indicates the optimum cleaning time when the teeth are vigorously cleaned with a toothbrush wherein the colored foam generated by the dentifrice at the beginning in at least about 20 seconds becomes white or only pale in color.

2. A method as claimed in claim 1, in which for a surfactant content of at least about 2.5% based on the total weight of the dentifrice, the dye content is sufficient to give a difference in lightness Δ L of about 10 to 30 during a normal brushing time.

3. A method as claimed in claim 2 in which the dye content is sufficient to give a difference in lightness Δ L from about 15 to 25.

4. A method as claimed in claim 1 in which the surfactant content is from about 2.5 to 8% based on the total weight of the dentifrice.

5. A method as claimed in claim 4 in which the surfactant content is from about 4 to 6% by weight.

6. A method as claimed in claim 1, in which the dye belongs to Class III/2 and/or Class IV/2 of the Common Market Directive.

7. A method as claimed in claim 1, in which the surfactant is an alkali metal salt of a fatty alcohol sulphate, alkane sulphonate, fatty acid tauride and/or amine oxide.

8. A method as claimed in claim 1, in which the surfactant is a mixture of the sodium salt of lauryl alcohol sulphate and the sodium salt of myristic acid tauride in a weight ratio of about 3:2.

* * * * *